(12) United States Patent
Ellis et al.

(10) Patent No.: US 11,224,344 B2
(45) Date of Patent: Jan. 18, 2022

(54) METHOD AND SYSTEM FOR DETERMINATION OF CORE BODY TEMPERATURE

(71) Applicant: James Foody, Co. Sligo (IE)

(72) Inventors: Nathan Ellis, Glanmire (IE); James Foody, Glanmire (IE)

(73) Assignee: James Foody, Co. Sligo (IE)

( * ) Notice: Subject to any disclaimer, the term of this patent is extended or adjusted under 35 U.S.C. 154(b) by 607 days.

(21) Appl. No.: 15/682,292

(22) Filed: Aug. 21, 2017

(65) Prior Publication Data

US 2018/0242850 A1    Aug. 30, 2018

Related U.S. Application Data

(60) Provisional application No. 62/532,306, filed on Jul. 13, 2017, provisional application No. 62/417,183, (Continued)

(51) Int. Cl.
| | |
|---|---|
| *A61B 5/01* | (2006.01) |
| *G01K 7/42* | (2006.01) |
| *G01K 13/20* | (2021.01) |
| *G16H 40/67* | (2018.01) |
| *A61B 5/00* | (2006.01) |
| *A61B 5/02* | (2006.01) |
| *A61B 5/0205* | (2006.01) |
| *A61B 5/026* | (2006.01) |

(Continued)

(52) U.S. Cl.
CPC .............. *A61B 5/01* (2013.01); *A61B 5/0008* (2013.01); *A61B 5/026* (2013.01); *A61B 5/02007* (2013.01); *A61B 5/02055* (2013.01); *A61B 5/4857* (2013.01); *A61B 5/7282* (2013.01); *G01K 1/20* (2013.01); *G01K 7/42* (2013.01); *G01K 13/20* (2021.01); *G16H 40/67* (2018.01); *A61B 5/021* (2013.01); *A61B 5/0533* (2013.01); *A61B 5/11* (2013.01); *A61B 2562/0219* (2013.01); *A61B 2562/0271* (2013.01); *Y02A 90/10* (2018.01)

(58) Field of Classification Search
None
See application file for complete search history.

(56) References Cited

U.S. PATENT DOCUMENTS

| | | |
|---|---|---|
| 6,220,750 B1 | 4/2001 | Palti |
| 6,499,877 B2 | 12/2002 | Pompei |

(Continued)

FOREIGN PATENT DOCUMENTS

| | | | | |
|---|---|---|---|---|
| WO | 2013121762 A1 | 8/2013 | | |
| WO | WO-2014207484 A1 * | 12/2014 | ........... | A61B 5/0008 |

*Primary Examiner* — Etsub D Berhanu
(74) *Attorney, Agent, or Firm* — Jeffrey Schox

(57) ABSTRACT

Embodiments of a method and/or system for characterizing physiological metrics can include: collecting temperature data from a set of temperature sensors associated with at least one heat flux channel of a temperature monitoring device configured to couple to an exterior region of a user; extracting a perfusion parameter based on the temperature data; determining a core body temperature measurement (and/or other suitable physiological metric) based on the perfusion parameter; and/or characterizing a user condition (e.g., fever) based on the core body temperature measurement (and/or other suitable physiological metric).

7 Claims, 11 Drawing Sheets

Related U.S. Application Data filed on Nov. 3, 2016, provisional application No. 62/377,531, filed on Aug. 19, 2016, provisional application No. 62/377,530, filed on Aug. 19, 2016.

(51) Int. Cl.
  *G01K 1/20* (2006.01)
  *A61B 5/021* (2006.01)
  *A61B 5/0533* (2021.01)
  *A61B 5/11* (2006.01)

(56) References Cited

U.S. PATENT DOCUMENTS

| | | | |
|---|---|---|---|
| 6,821,249 B2 * | 11/2004 | Casscells, III | A61B 5/01 128/898 |
| 6,827,487 B2 | 12/2004 | Baumbach | |
| 7,785,266 B2 | 8/2010 | Fraden | |
| 8,845,187 B2 | 9/2014 | Klewer et al. | |
| 2002/0114375 A1 | 8/2002 | Pompei | |
| 2004/0076215 A1 | 4/2004 | Baumbach | |
| 2007/0055171 A1 | 3/2007 | Fraden | |
| 2007/0161921 A1 * | 7/2007 | Rausch | G16H 40/63 600/549 |
| 2007/0191729 A1 * | 8/2007 | Park | A61B 5/107 600/551 |
| 2008/0071189 A1 * | 3/2008 | Yarden | A61B 5/01 600/549 |
| 2009/0016404 A1 * | 1/2009 | Wang | G01K 13/20 374/141 |
| 2009/0306536 A1 * | 12/2009 | Ranganathan | A61B 5/6804 600/549 |
| 2009/0306638 A1 | 12/2009 | Hillely et al. | |
| 2011/0317737 A1 | 12/2011 | Klewer et al. | |
| 2012/0128024 A1 * | 5/2012 | Tsuchida | G01K 13/002 374/29 |
| 2014/0169400 A1 * | 6/2014 | Baarman | A61B 5/01 374/45 |
| 2015/0305688 A1 * | 10/2015 | Rath | A61B 5/7275 600/301 |
| 2015/0313484 A1 * | 11/2015 | Burg | A61B 5/0404 600/301 |
| 2016/0313193 A1 | 10/2016 | Nakagawa et al. | |
| 2017/0016778 A1 | 1/2017 | Nakagawa et al. | |

* cited by examiner

METHOD AND SYSTEM FOR DETERMINATION OF CORE BODY TEMPERATURE

CROSS-REFERENCE TO RELATED APPLICATIONS

This application claims the benefit of U.S. Provisional Application Ser. No. 62/532,306, filed on 13 Jul. 2017, U.S. Provisional Application Ser. No. 62/417,183 filed on 3 Nov. 2016, U.S. Provisional Application Ser. No. 62/377,531 filed on 19 Aug. 2016, U.S. Provisional Application Ser. No. 62/377,530 filed on 19 Aug. 2016, which are each incorporated herein in their entireties by this reference.

TECHNICAL FIELD

This invention relates generally to the medical monitoring field, and more specifically to a method and system for accurately characterizing temperature parameters.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Overview

Figure 1A:
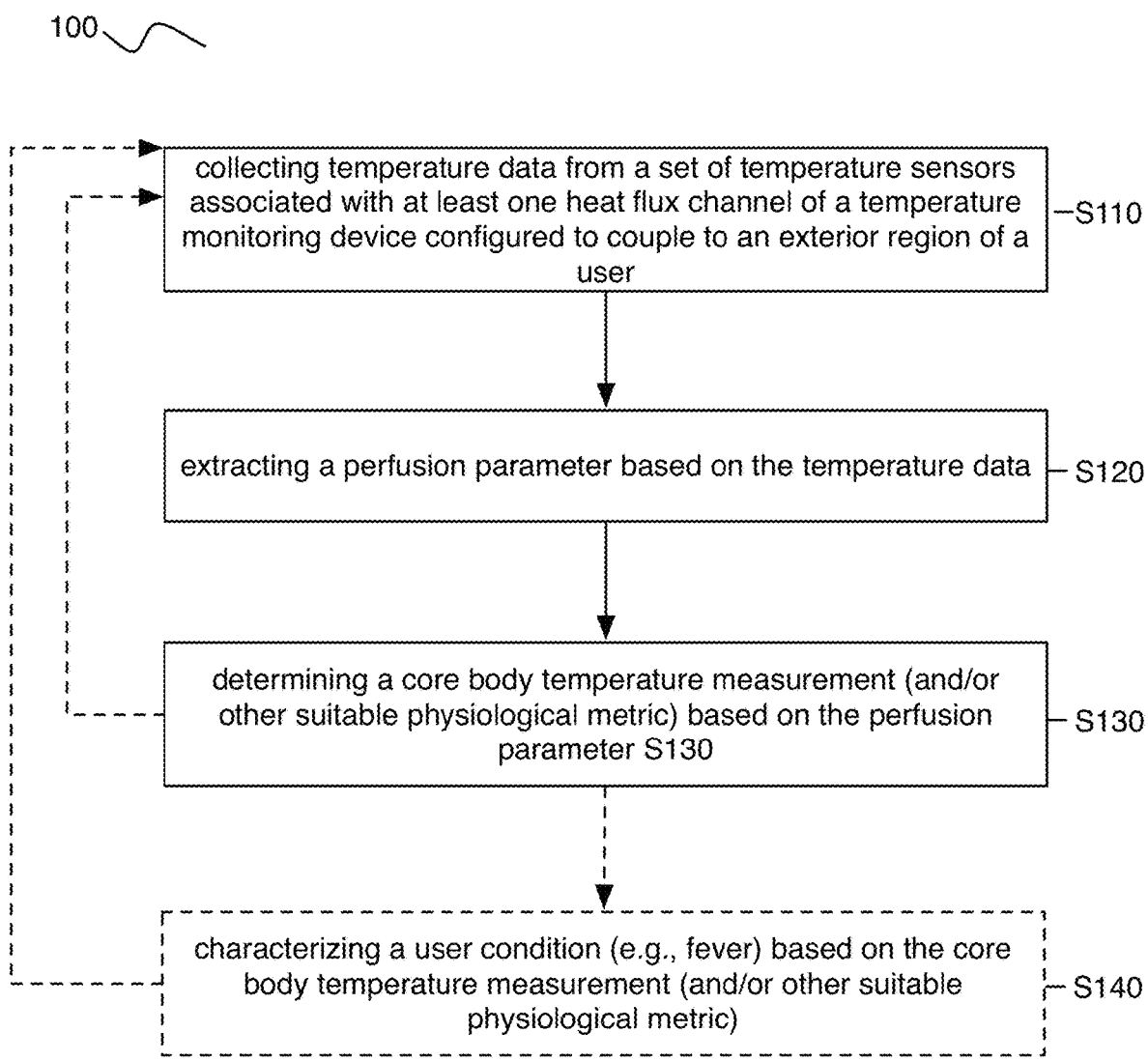
FIG. 1A-1B depict embodiments of a method for characterizing core body temperature.
Figure 1B:
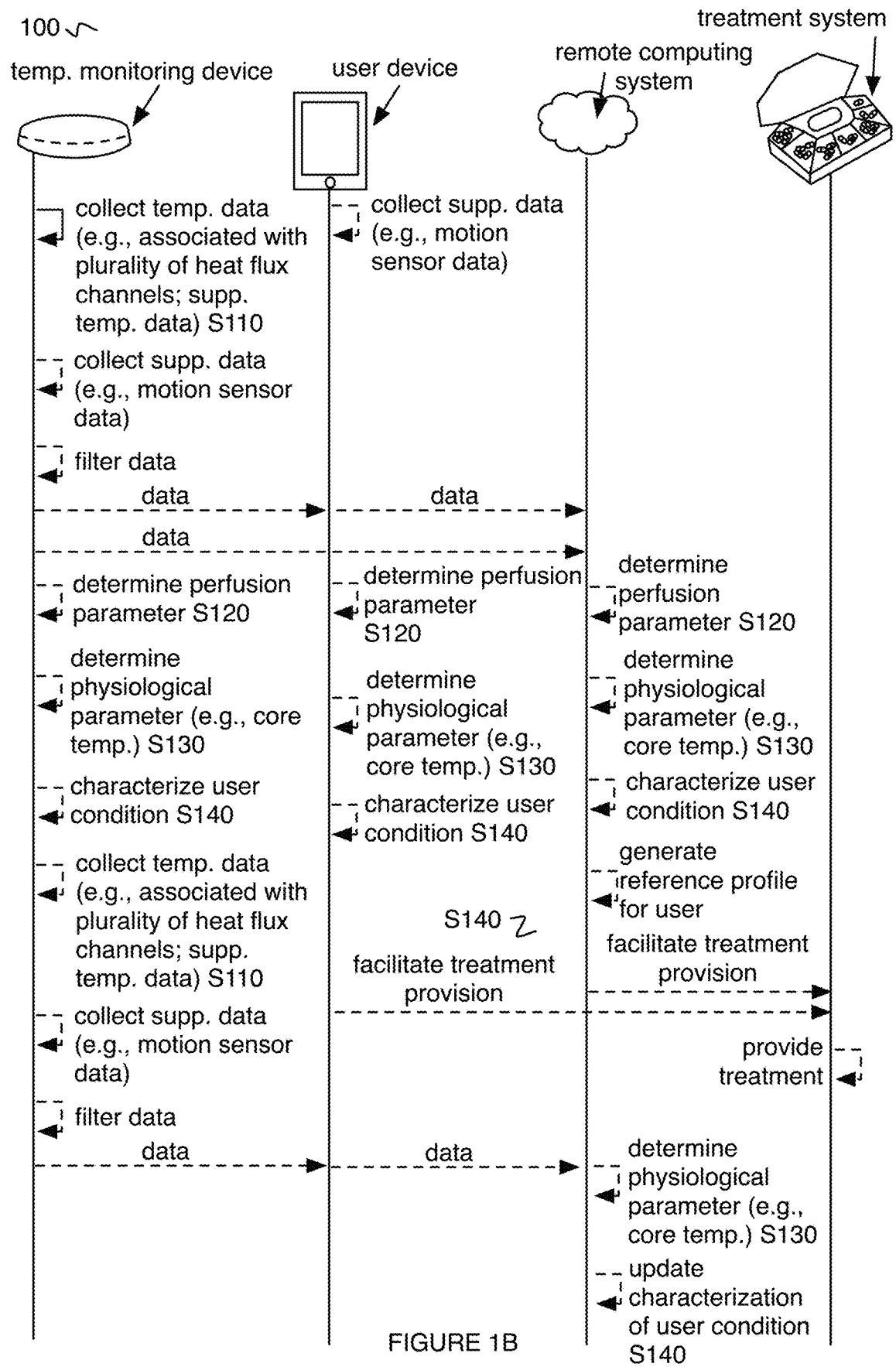
Figure 2:
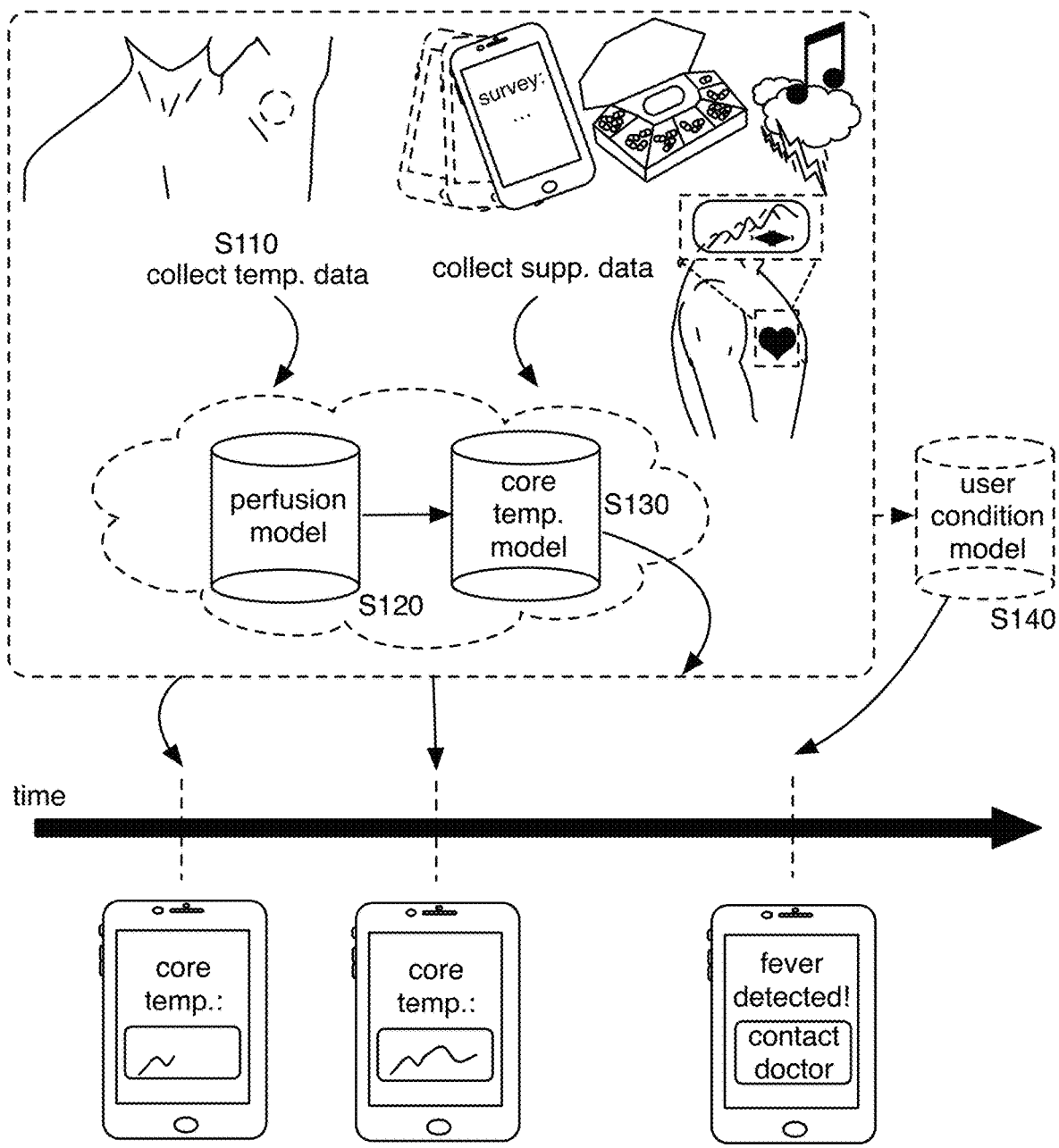
FIG. 2 depicts an embodiment of a method for characterizing core body temperature.

As shown in FIGS. 1A-1B and 2, embodiments of a method 100 for characterizing physiological metrics can include: collecting temperature data from a set of temperature sensors associated with at least one heat flux channel of a temperature monitoring device configured to couple to a region of a user S110; extracting a perfusion parameter based on the temperature data S120; and determining a core body temperature measurement (and/or other suitable physiological metric) based on the perfusion parameter S130. Additionally or alternatively, embodiments of the method 100 can include: characterizing a user condition (e.g., fever) based on the core body temperature measurement (and/or other suitable physiological metric) S140; and/or any other suitable processes.

Embodiments of the method 100 and/or system 200 can function to non-invasively characterize core body temperature (and/or other suitable parameters) over time for a user in an accurate manner (e.g., by accounting for dynamic changes in perfusion, thermal properties, and/or other suitable properties of the tissue and/or material, etc.), such as based on temperature data from a temperature monitoring device including a plurality of heat flux channels associated with different measurement sites (e.g., at different exterior skin regions of the user, etc.). Embodiments can additionally or alternatively function to characterize user conditions (e.g., early fever detection) based on the series of core body temperature measurements (e.g., in a manner that accounts for circadian variation and/or other suitable variations in core body temperature) and/or other suitable parameters (e.g., accounting for variables such as physical activity level, which can affect core body temperature measurements, etc.), where such characterization can facilitate real-time, responsive healthcare for improving a state of the user condition (e.g., through facilitating initial treatment prescription, continuous evaluation of prescribed treatments, updating of treatments, etc.).

In examples, embodiments of the method and/or system can be used in the context of characterizing (e.g., detecting, diagnosing, evaluating, etc.), treating, and/or otherwise performing processes related to user conditions, which can include at least one of: symptoms, causes, diseases, disorders, and/or any other suitable aspects associated with conditions. User conditions preferably include a fever-associated condition, which can include any one or more of: fever (e.g., continuous fever, intermittent fever, remittent fever, Pel-Ebstein fever, fevers with other suitable temperature patterns, etc.), infectious diseases (e.g., malaria, gastroenteritis, Lyme disease, infectious mononucleosis, Ebola, HIV infection, influenza, etc.), cancer (e.g., kidney cancer, leukemia, lymphomas, etc.), immunological diseases (e.g., inflammatory bowel diseases, lupus erythematosus, sarcoidosis, Kawasaki disease, Horton disease, granulomatosis with polyangiitis, Still disease, autoimmune hepatitis, relapsing polychondritis, etc.), immune reactions (e.g., incompatible blood products, incompatible organ products, etc.), skin conditions (e.g., boils, abscess, other skin inflammations, etc.), tissue destruction (e.g., associated with infarction, crush syndrome, hemolysis, surgery, rhabdomyolysis, cerebral bleeding, etc.), metabolic disorders (e.g., Fabry disease, gout, porphyria, etc.), and/or other suitable conditions related to fever. Additionally or alternatively, user conditions can include and/or be otherwise associated with: fertility (e.g., female health tracking, female cycle tracking, pregnancy planning, etc.), cardiovascular conditions (e.g., conditions related to blood pressure, vasodilation, vasoconstriction, vasocongestion, etc.), patient monitoring (e.g., in-home monitoring, monitoring in a hospital setting, continuous monitoring, etc.), sepsis, diseases affecting core temperature, treatment response evaluation (e.g., physiological response to treatments such as medication), disease research (e.g., using core temperature data to provide insights into causes, symptoms, and/or treatments for disease), ambulatory settings (e.g., ICU settings), sports medicine (e.g., athlete performance tracking, athlete health tracking), at-risk professions (e.g., astronauts, fire fighters, professionals at-risk of heat exhaustion and/or heat stroke, etc.), and/or other suitable conditions and/or applications.

One or more instances and/or portions of the method 100 and/or processes described herein can be performed asynchronously (e.g., sequentially), concurrently (e.g., in parallel; concurrently on different threads for parallel computing to improve system processing ability for characterizing core body temperature, user conditions, and/or other suitable aspects for one or more users, temperature monitoring devices, components of temperature monitoring devices such as a plurality of heat flux channels; etc.), in temporal relation to a trigger event, and/or in any other suitable order at any suitable time and frequency by and/or using one or more instances of the system 200, elements, and/or entities described herein. Embodiments of the system 200 can include one or more: heat flux channels (e.g., a multi-flux system including heat flux channels associated with different measurement sites, etc.), temperature sensors (e.g., pairs of temperature sensors thermally coupled to different heat flux channels, etc.), thermal cages (e.g., thermally coupled to and arranged around heat flux channels for preventing thermal leakage into and/or out of the heat flux channels; etc.), supplemental sensors (e.g., motion sensors), processing and control subsystems (e.g., integrated with the temperature monitoring device; remote processing systems, such as in the cloud; mobile computing devices such as smartphones, laptops, tablets; etc.), mounting system (e.g., charging hub, casing, docking station, etc.), substrates, thermal gap fillers, thermal insulation, housings (e.g., disk-shaped form factor), cooling features, heat sinks, supplemental thermal features, and/or any other suitable components.

The components of the system 200 can be physically and/or logically integrated in any manner. For example, the system components can be applied with any suitable distribution of performing portions of the method 100. In a specific example, characterizing core body temperature (and/or other suitable parameters) can be performed at one or more of a: remote computing system (e.g., a remote server), a user computing device (e.g., mobile smartphone, laptop, tablet, etc.), a temperature monitoring device (e.g., where initial temperature data was collected, etc.). Additionally or alternatively, the system 200 and/or associated components can be configured in any suitable manner described in and/or analogous to U.S. application Ser. No. 15/682,138 filed 21 Aug. 2017 titled "SYSTEM AND METHOD FOR MONITORING CORE BODY TEMPERATURE" and U.S. Provisional App. No. 62/532,306 filed 13 Jul. 2017. However, the method 100 and/or system 200 can be configured in any suitable manner.

2. Benefits

The method 100 and/or system 200 can confer several benefits over conventional approaches. For example, conventional temperature measurement approaches (e.g., rectal probes, one-time use ingestible pills, thermometers, etc.) can be expensive, inconvenient, possess limited accuracy, and/or invasive. In another example, fever detection and/or other suitable characterizations of user conditions associated with temperature parameters can be unsuitable for providing optimal, responsive healthcare (e.g., treatments based on user condition trends, user condition severity, real-time user condition characterization, continuous measurements associated with user conditions, etc.). Examples of the method 100 and/or system 200 can confer solutions to at least the challenges described above.

First, the technology can improve the technical fields of at least computational characterization (e.g., modeling, estimation, analysis, etc.) of core body temperature, associated user conditions, associated user behaviors (e.g., affecting core body temperature, etc.), and/or other associated aspects, digital medicine, computer networks (e.g., for improving collection, storage, retrieval, analysis, and/or other usage of temperature data and/or other suitable data across a plurality of users, user characteristics, steady-state conditions, transient conditions, temperature monitoring devices; through providing a software development kit leveraging portions of the technology; etc.), and/or other relevant fields. The technology can continuously collect and utilize specialized datasets (e.g., temperature data associated with sets of heat flux channels, motion sensor data, mobile computing device sensor data, supplemental data including contextual data about the user, etc.) associated with non-generalized computing devices in order to characterize core body temperature and associated user conditions (e.g., through improving the understanding of correlations between core body temperature, conditions affecting core body temperature, relevance to different user conditions, etc.).

Second, the technology can confer improvements in accuracy of core body temperature measurements (e.g., absolute core body temperatures of deep organs, tissue, arterial blood flow, etc.) and associated characterizations of user conditions such as fever (e.g., where accurate diagnosis can require accurate core body temperature determination). For example, the technology can leverage temperature data sampled from a plurality of temperature sensors associated with one or more heat flux channels of a non-invasive temperature monitoring device that can account for heat gains from the device itself, heat losses to the ambient environment and lateral heat flux, and/or other heat gains or losses to and/or from the temperature sensors and/or other components. In a specific example, the technology can account for the effects on temperature parameters (e.g., core body temperature, etc.) from the dynamic changes in perfusion (e.g., effective thermal resistivity of tissue; of non-organic materials, such as in industrial applications; etc.). In another specific example, the technology can account for the effects on temperature parameters from contextual variables (e.g., time of day, physical activity, medical history, location, user demographic, etc.), such as by normalizing current core body temperature measurements according to a reference circadian core temperature profile (e.g., for the specific user, etc.). In another specific example, the technology can leverage a series of core body temperature measurements (and/or other suitable measurements) determined over time to characterize trends and/or other patterns for evaluating user conditions.

Third, the technology can transform entities (e.g., temperature monitoring devices, processing systems, users, user conditions, etc.) into different states or things. For example, the technology can facilitate accurate and early detection of fever, which can facilitate treatment provision to prevent and/or ameliorate associated user conditions, thereby transforming the health of the user. In another example, the technology can transform biological signals from the user (e.g., temperature signals; motion signals) into temperature data (e.g., through temperature sensors) usable in generating core body temperature models and/or user condition models. In another example, outputs from the technology can be used to modify temperature monitoring device operation (e.g., updating suitable firmware and/or software for the temperature monitoring device in relation to power consumption, data processing, sensor sampling, and/or other suitable aspects, based on evaluation of outputs of the temperature monitoring device and/or other temperature monitoring devices, etc.). In another example, outputs from the technology can be used to control therapy to promote therapies (e.g., where control instructions for therapy systems can be based on core body temperature measurements determined by the technology), thereby transforming the therapy system.

Fourth, the technology can leverage specialized computing devices (e.g., temperature monitoring devices, such as those described in U.S. application Ser. No. 15/682,138, filed 21 Aug. 2017 titled "SYSTEM AND METHOD FOR MONITORING CORE BODY TEMPERATURE", which is herein incorporated in its entirety by this reference; mobile or non-mobile computing devices with location sensors, motion sensors, physical activity monitoring capabilities, processing capabilities for core body temperature characterization; etc.) in collecting and processing non-generic datasets for evaluating temperature-associated parameters. The technology can, however, provide any other suitable benefit(s) in the context of characterizing core body temperature and/or other suitable parameters.

3.1 Collecting Temperature Data.

Block S110 recites: collecting temperature data from a set of temperature sensors associated with at least one heat flux channel of a temperature monitoring device. Block S110 can function to obtain temperature data for subsequent processing to determine core body temperature. In a specific example, collecting temperature data can include collecting temperature data from one or more temperature monitoring devices described in and/or analogous to U.S. application Ser. No. 15/682,138, filed 21 Aug. 2017 titled "SYSTEM AND METHOD FOR MONITORING CORE BODY TEMPERATURE", which is herein incorporated in its entirety by this reference.

Temperature data preferably includes data sampled at one or more temperature sensors (e.g., of a temperature monitoring device, of a user computing device, etc.). The temperature sensors are preferably thermally coupled to one or more heat flux channels (e.g., associated with a temperature change from a measurement site proximal a user external region), but can additionally or alternatively be thermally coupled to and/or otherwise coupled to: insulating materials, conductive materials, cooling features, heat sinks, other thermal features, other system components, and/or any other suitable components. The temperature sensors can be associated with any suitable channel thermal resistances, any suitable couplings to a corresponding processing and control subsystem, and/or any suitable electrical, thermal, and/or physical couplings to any components of the system. In an example, Block S110 can include collecting temperature data from a first and a second set of temperature sensors respectfully coupled to a first and a second heat flux channel, where the temperature data is indicative of temperature changes through the first and the second heat flux channels during a time period associated with coupling of the temperature monitoring device to the user. In this or other examples, Block S110 can include collecting additional temperature data associated with the time period from a third set of temperature sensors (e.g., thermally coupled to a third heat flux channel of the temperature monitoring device), and/or any number of temperature sensors associated with any number of heat flux channels.

Regarding Block S110, additionally or alternatively temperature data can include any one or more of: temperature associated with a temporal indicator (e.g., time, time period, etc.), aggregate temperature data (e.g., average temperature, median temperature), temperature change parameters (e.g., parameters associated with difference in temperatures, etc.), temperature patterns (e.g., trends over time), temperature associated with a single temperature sensor, temperature associated with a plurality of temperature sensors, temperature associated with steady-state conditions (e.g., while the user is at rest, etc.), temperature associated with transient conditions (e.g., while the user is performing a physical activity, etc.), reference temperature data (e.g., historic temperature data for the user and/or other suitable users; predetermined temperature data; reference temperature data for use in determining core body temperature and/or other suitable parameters, for user in characterizing user conditions, etc.), and/or any other suitable types of temperature data. In an example, temperature data from a first set of sensors can temporally correspond to temperature data from a second set of sensors. In a specific example, a first initial temperature measurement from a first temperature sensor thermally coupled to a first heat flux channel (e.g., at a beginning region of the heat flux channel associated with a first measurement site of the user, etc.) can be for a time substantially matching a time of sampling of a second initial temperature measurement from a second temperature sensor thermally coupled to a second heat flux channel (e.g., at a beginning region associated with a second measurement site of the user, etc.). Similarly, temperature measurements from temperature sensors arranged at any suitable region of a heat flux channel (e.g., at an end region, at an intermediary region) can have any suitable temporal correspondence across heat flux channels, devices, users, and/or any other suitable entities. In another example, temperature data can include supplemental temperature data for measuring cross-talk between heat flux channels and/or temperature sensors (e.g., where supplemental temperature data can be collected from temperature sensors arranged between heat flux channels, etc.), for measuring heat gradients across portions of the temperature monitoring device (e.g., where supplemental temperature data can be collected from temperature sensors arranged proximal perimeter regions of substrates supporting heat flux channels, arranged around heat flux channels, and/or arranged at any suitable region; etc.), for performing other adjustments (e.g., normalizations, etc.) to temperature measurements from temperature sensors for accounting for any suitable variability, and/or for any other suitable purpose.

Block S110 preferably includes collecting temperature data from a temperature monitoring device (e.g., including a set of heat flux channels), but can additionally or alternatively include collecting temperature-associated data from: mobile computing devices (e.g., including temperature sensors), supplementary medical devices, third party databases (e.g., databases including medical records, personal temperature measurements, etc.), and/or any other suitable entity. Temperature data can be received at a remote computing system (e.g., corresponding to a first party associated with the temperature monitoring device; corresponding to a third party, etc.), at a processing system of the temperature monitoring device, at a user computing device, and/or any other suitable entity. Receiving (and/or transmitting) temperature data (and/or other suitable data) can be through any one or more of wired communication (e.g., through communication pins, such as of a temperature monitoring device; Ethernet components; powerline components; etc.), wireless communication (e.g., Bluetooth such as Bluetooth Low Energy; WiFi; Zigbee; Z-wave; radios; radiofrequency; infrared; magnetic induction; etc.) and/or through any other suitable communication means. In a variation, collecting temperature data can include directly receiving temperature data from the source at which the temperature data was sampled (e.g., wirelessly receiving the temperature data from a WiFi communication module of the temperature monitoring device, etc.). In another variation, collecting temperature data can include indirectly receiving the temperature data. In a specific example, Block S110 can include: transmitting the temperature data from the temperature monitoring device to a user computing device (e.g., a mobile smartphone, through Bluetooth); and receiving the temperature data at a remote server from the user computing device. In another specific example, Block S110 can include: receiving the temperature data at a mounting system (e.g., through a physical connection between the docking station and the temperature monitoring device), and receiving the temperature data at a remote server from the mounting system.

In variations of Block S110, collecting temperature data can be performed: actively (e.g., transmitting requests to temperature monitoring devices for temperature data; etc.), passively (e.g., receiving temperature data pushed by the temperature monitoring device without request; etc.), according to computer-implemented data collection rules, and/or in any other suitable manner. In examples, computer-implemented data collection rules can specify the manner (e.g., when, such as sampling and/or collection frequency; how, such as wireless communication; what, such as amount and/or types of temperature data; etc.) in which temperature data (and/or other suitable data) is collected. Block S110 can include applying different data collection rules for different: times (e.g., collecting temperature data at different frequencies based on a circadian core temperature profile for the user, such as collecting temperature data at a higher frequency during time periods where core body temperature historically fluctuates for the user; etc.), steady-state and/or transient conditions (e.g., transmitting temperature data collected during steady-state conditions while filtering out temperature data collected during transient conditions; controlling the temperatures sensors to sample at a greater frequency during transient conditions; etc.), users (e.g., adjusting collection frequency based on severity of user condition of the user, such as in response to potential early detection of fever; adjusting temperature collection parameters based on demographic such as age; etc.), temperature monitoring devices (e.g., different temperature collection parameters for different types and/or versions of temperature monitoring devices, such as for different devices with different numbers of temperature sensors and/or heat flux channels), and/or for any other varying conditions. Additionally or alternatively, applying data collection rules can be performed in any manner. However, Block S110 can be performed in relation to any suitable components through any suitable communication means.

Block S110 can be performed at predetermined time intervals (e.g., collecting and/or sampling temperature data continuously, every second, minute, hour, day, etc.), in response to and/or concurrently with a trigger event (e.g., a threshold amount of temperature data stored at the temperature monitoring device; unexpected temperature data values; a request for the temperature data, such as from the user and/or a first party; etc.) and/or at any suitable frequency or time in any suitable temporal relationship to other portions of the method 100. In an example, Block S110 can be performed in substantially real-time, where collecting temperature data can include receiving temperature data (e.g., at a mobile computing device Bluetooth paired with the temperature monitoring device) in response to sampling of the temperature data at a temperature sensor. In another example, Block S110 can include filtering out temperature data based on contextual data (e.g., motion sensor data, location data, etc.) and/or any other suitable data types described herein. In a specific example, the method 100 can include: evaluating a motion-related condition (e.g., threshold amount of movement; orientation conditions; threshold level of physical activity; etc.) based on motion sensor data sampled at an motion sensor (e.g., accelerometer) of the temperature monitoring device and/or other suitable device (e.g., mobile computing device) during a time period (e.g., a time period associated with sampling of the temperature data); in response to failure to satisfy the motion-related condition, filtering out the temperature data; and in response to satisfaction of the motion-related condition, performing portions of the method 100 (e.g., subsequent extracting of the perfusion parameter, determining of core body temperature, characterizing of user conditions, etc.). However, Block S110 can be performed at any suitable time and frequency.

In a variation, Block S110 can include storing the collected temperature data, which can function to store the data in an organized manner to improve subsequent retrieval and analysis of the data. In examples, temperature data can be stored in association with: user accounts (e.g., identifying the user for which the temperature data was sampled; for enabling the corresponding user to view and/or otherwise use the temperature data; identifying care providers and/or other individuals associated with the user; etc.), temperature monitoring device identifier (e.g. identifying the device at which the temperature data was sampled; identifying other temperature monitoring devices owned by the user; etc.), time (e.g., associating the temperature data with specific time periods, such as based on hour, day, week, circamensal rhythm, circadian rhythm; etc.), user type (e.g., based on user subgroup associated with specific demographics, user conditions; etc.) and/or any other suitable varying conditions.

In another variation, Block S110 can include pre-processing the collected temperature data. Pre-processing temperature data and/or any other suitable data types described herein can include any one or more of: extracting features (e.g., temperature-related patterns and/or trends over time; aggregate features from processing temperature data across multiple temperature sensors; etc.), performing pattern recognition on data, fusing data from multiple sources, combination of values (e.g., averaging temperature data from multiple sensors, averaging temperature data collected over time, etc.), normalization (e.g., based on historic temperature data, reference temperature data associated with other users, etc.), performing statistical estimation on data (e.g. ordinary least squares regression, non-negative least squares regression, principal components analysis, ridge regression, etc.), weighting (e.g., weighting different temperature data based on suitable varying conditions such as time, steady-state conditions, transient conditions, etc.), validating (e.g., with other temperature sensors), filtering (e.g., based on motion sensor data and/or other sensor data indicative of perturbations; for baseline correction; etc.), noise reduction, smoothing, filling (e.g., Kalmann filtering; gap filling), model fitting, binning, windowing, clipping, transformations, mathematical operations (e.g., derivatives, moving averages, summing, subtracting, multiplying, dividing, etc.), interpolating, extrapolating, clustering, visualizing (e.g., for display to a user, to a care provider, etc.), and/or other suitable processing operations. In an example, processing data can include associating different temperature data based on a common and/or overlapping temporal indicator (e.g., associated with the sampling of the temperature data, etc.) which can enable data collected from multiple sources (e.g., across multiple heat flux channels) during a common temporal indicator to be processed and/or analyzed together. However, collecting temperature data can be performed in any suitable manner.

3.2 Determining a Perfusion Parameter.

Figure 3:
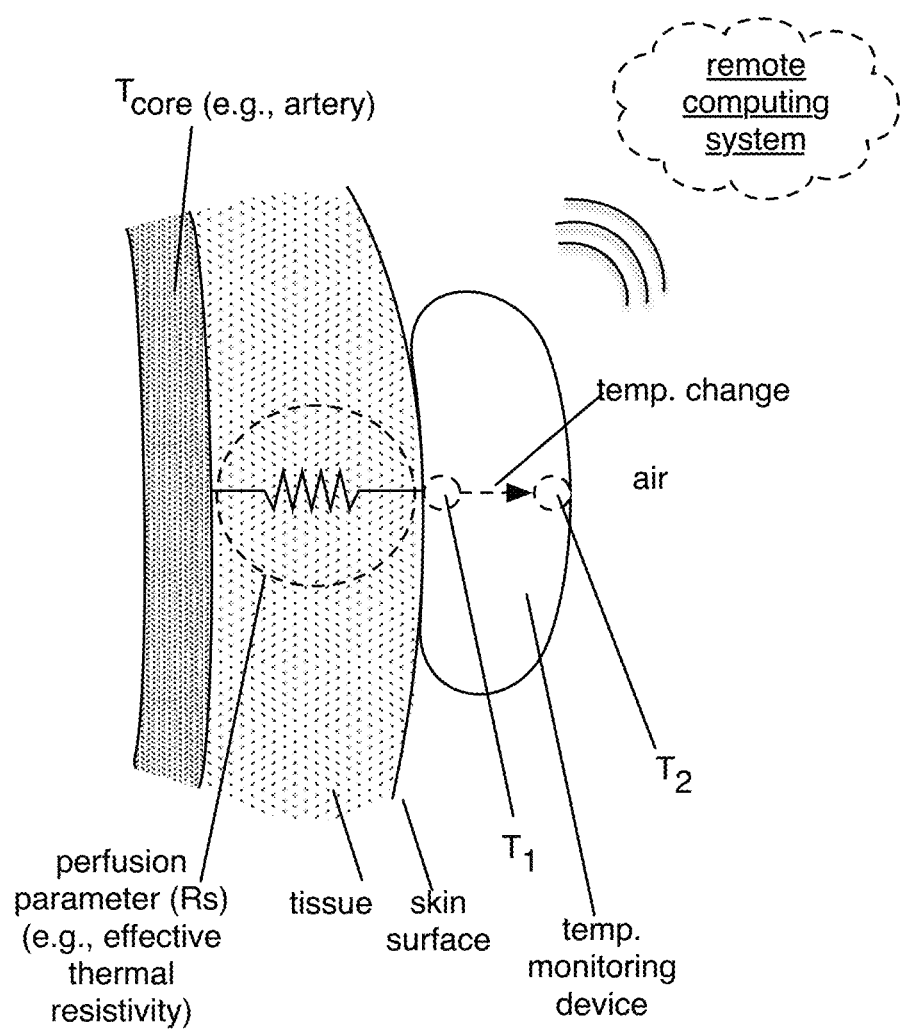
FIG. 3 depicts a schematic representation of a variation of characterizing body temperature based on a perfusion parameter.
Figure 7A:
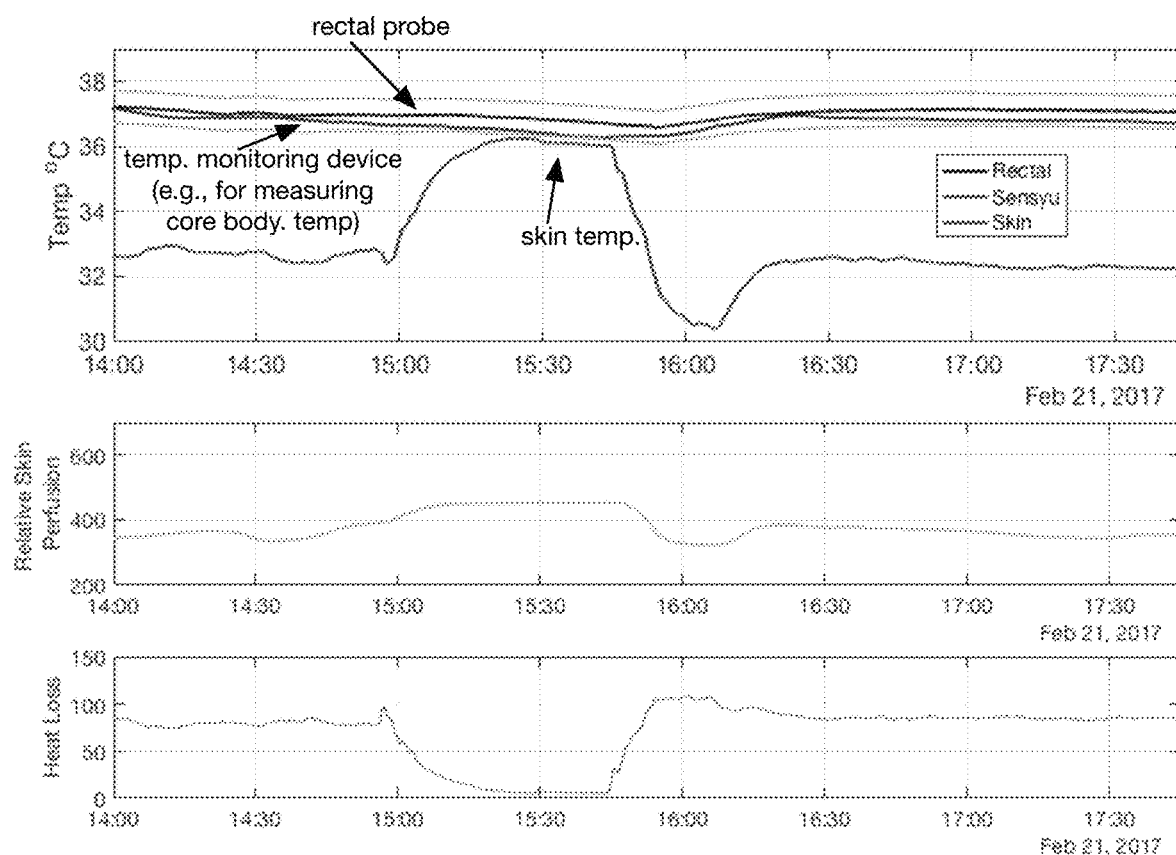
FIG. 7A-7B depict a graph representation of a specific example of core body temperature measurements.
Figure 7B:
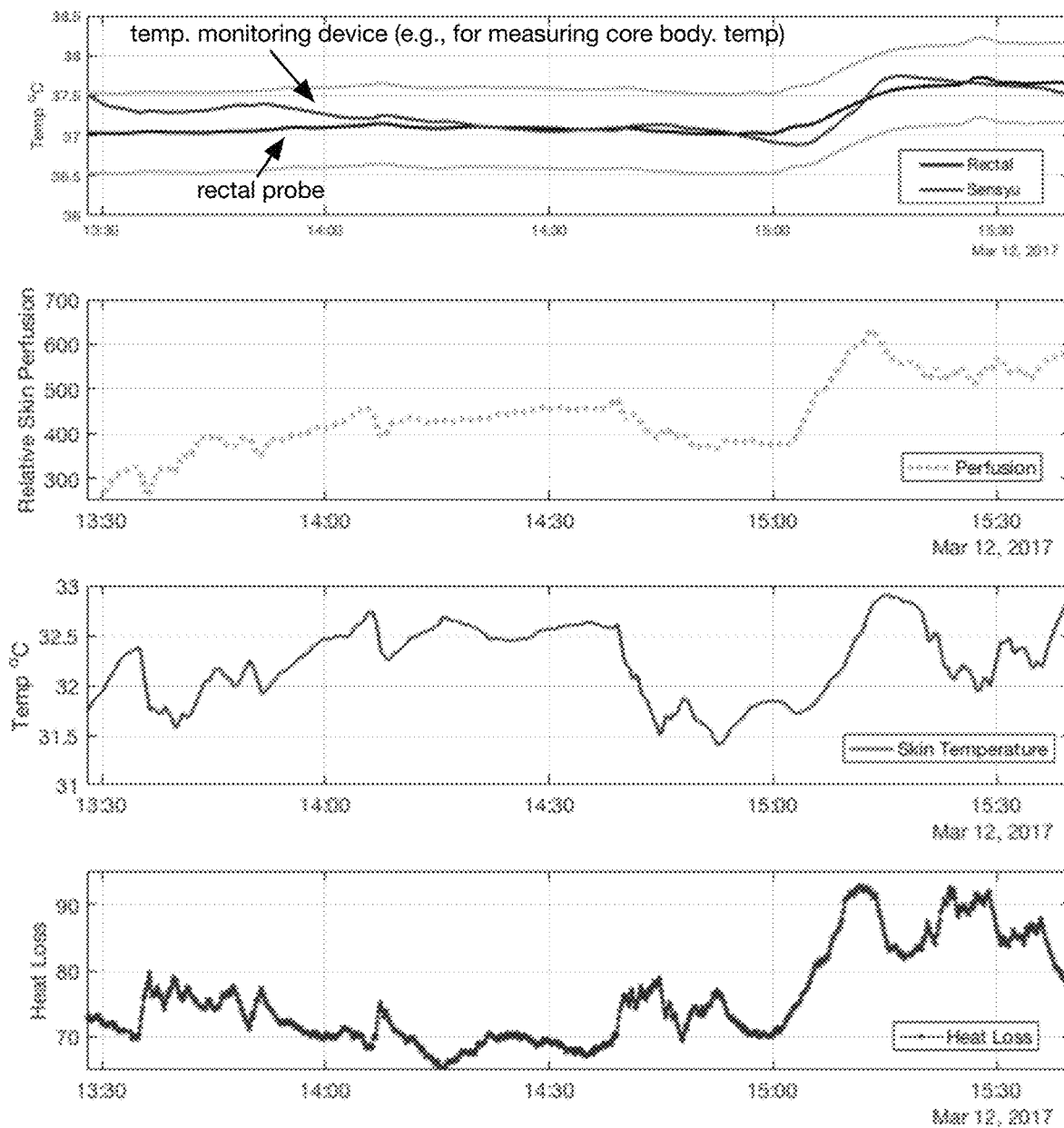

Block S120 recites: extracting a perfusion parameter based on the temperature data, which can function to account for perfusion and/or other related phenomena in relation to characterizing core body temperature and/or other parameters. Perfusion parameters are preferably related to thermal resistivity of tissue and/or other physiological regions (e.g., of humans, animals; as shown in FIG. 3, etc.), but can additionally or alternatively be related to thermal resistivity of non-organic materials, and/or any other suitable aspects associated with perfusion. In an example, as shown in FIG. 7A, perfusion parameters can vary or stay consistent relative different disturbances, such as where, in response to skin temperature increase (e.g., a user rolling over in bed and covering a temperature monitoring device) at 15:00, heat loss can drop with relatively small change in perfusion parameter values (e.g., given that ambient conditions have changed but not the user's underlying physiology). In another example, as shown in FIG. 7B, with increasing core body temperature (e.g., due to exercising), perfusion can increase (e.g., where blood flow into the skin network can increase to enable radiative heat loss to the environment to help cool the user, such as in vasodilation; etc.), leading to increases in skin temperature and heat loss (e.g., from the skin network). In another example, vasoconstriction (e.g., for reducing heat loss when a user psychologically feels they are colder due to a new fever set-point; etc.) can occur in response to onset of infection, which can be detected by a decrease in perfusion parameter values (e.g., where skin temperature and heat loss decreases while core body temperature increases). However, Block S120 can include determining perfusion parameters over time with any suitable relationship to temperature parameters for any suitable conditions.

Perfusion parameters can include any one or more of: current perfusion, perfusion associated with a temporal indicator (e.g., time, time period, over time, etc.), aggregate perfusion parameters (e.g., median perfusion, average perfusion, etc.), changes in perfusion (e.g., vasodilation, vasoconstriction, vasocongestion), influencing factors (e.g., fat concentration; vascular network; vascular structure; hydration; sweat; physiological effects; etc.), perfusion during steady-state conditions, perfusion during transient conditions, thermal resistivity of non-organic materials and/or associated influencing factors (e.g., ambient conditions; environmental conditions; applied stimulus such as electrical, magnetic, photonic, mechanical stress; chemical reactivity; etc.), and/or any other suitable parameters associated with perfusion. In an example, perfusion parameters can be dynamically determined for different temporal indicators (e.g., different times, time periods, etc.), such as for temporal indicators corresponding to measurements of temperature data from temperature sensors (e.g., in relation to Block S110), but perfusion parameters can be otherwise temporally characterized.

Figure 4:
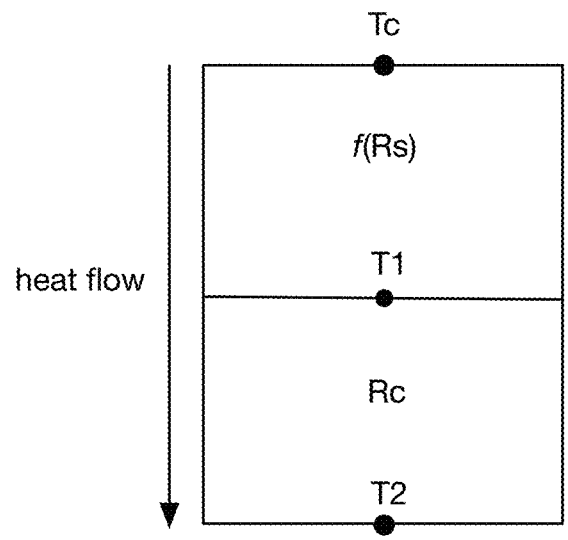
FIG. 4 depicts a schematic representation of a variation of determining a perfusion parameter.

As shown in FIG. 4, Block S120 can include passively estimating perfusion parameters (e.g., for environments where energetic disturbances are not applied to the target being sampled) based on:

$$Rs = f(Rc, Tc, T1, T2)$$

where a model can be described as:

$$Rs = Rc(Tc - T1)/(T1 - T2)$$

and where, Tc can be the core temperature (e.g., temperature beneath tissue; deep organ temperature; temperature associated with arterial and/or venous blood; temperature associated with cutaneous and/or subcutaneous tissue; etc.) and/or temperature beneath a material surface; T1 can be a temperature measurement of a first temperature sensor (e.g., for skin surface temperature; thermally coupled to a beginning region of a heat flux channel) and/or an interface temperature (e.g., non-organic applications); T2 can be a temperature measurement of a second temperature sensor (e.g., thermally coupled to an end region of the heat flux channel); Rc can be the thermal resistance of an insulating material between the first and second temperature sensors; and Rs can be the perfusion parameter (e.g., effective perfusion of tissue sample at and/or underneath the measurement site; effective thermal resistivity of target material and/or sample, such as for non-organic material; etc.). Additionally or alternatively, the parameters can be represented in the context of determining Tc as a function of Rs, where:

$$Tc = f(T1, T2, Rs, Rc)$$

where a model can be described as:

$$Tc = T1 + (Rs/Rc)/(T1 - T2)$$

In relation to Block S120, determining a perfusion parameter is preferably based on temperature data sampled at a plurality of temperature sensors corresponding to a plurality of heat flux channels, but can additionally or alternatively be based on temperature data from any suitable number of temperature sensors and heat flux channels (e.g., a single heat flux channel corresponding to a single measurement site; etc.).

Figure 5:
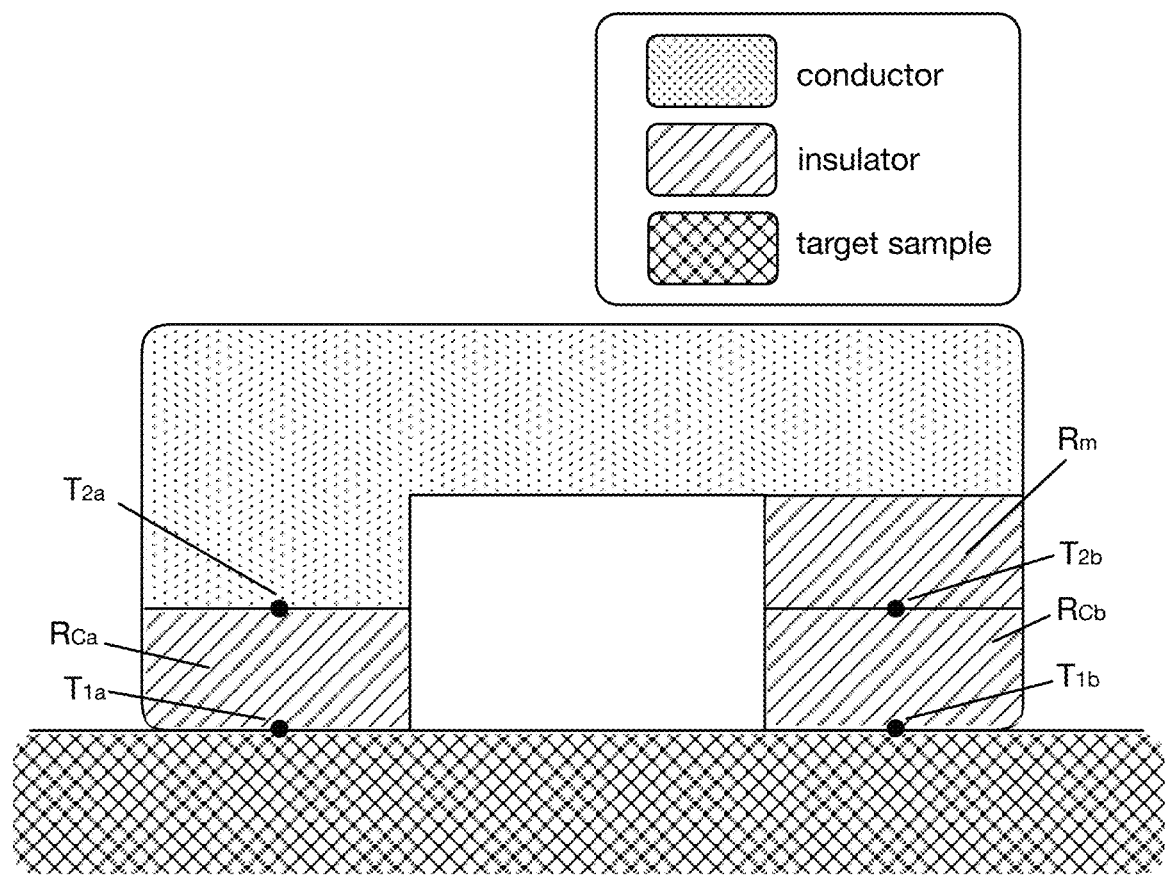
FIG. 5 depicts a schematic representation of a variation of determining a perfusion parameter.

Block S120 can include determining a perfusion parameter based on multiple measurement sites (e.g., corresponding to different heat flux channels, each thermally coupled to a different set of temperature sensors, etc.). Temperature data from multiple measurement sites can be used in processing a plurality of a simultaneous equations. In an example, as shown in FIG. 5, Rs can be determined based on simultaneous equations that can include:

Measurement Site 1: $Rs = f(Rca, Tc, T1a, T2a)$;

and

Measurement Site 2: $Rs = f(Rcb, Tc, T1b, T2b)$ where T1a and T2a can be the respective temperature measurements of a first and a second temperature sensor thermally coupled to a first heat flux channel (e.g., where the first temperature sensor is arranged proximal a beginning region of the heat flux channel; where the second temperature sensor is arranged proximal an end region of the heat flux channel; etc.); where T1b and T2b can be the respective temperature measurements of a third and a fourth temperature sensor thermally coupled to a second heat flux channel (e.g., where the third temperature sensor is arranged proximal a beginning region of the second heat flux channel; where the fourth temperature sensor is arranged proximal an end region of the second heat flux channel; etc.); Rca can be the thermal resistance of insulating material (and/or other material) thermally coupled to (e.g., arranged between) the first and the second temperature sensors; Rcb can be the thermal resistance of insulating material (and/or other material) thermally coupled to (e.g., arranged between) the third and the fourth temperature sensors.

In a variation of Block S120, Rs and Tc can be assumed to be equal across different measurement sites (e.g., where tissue and/or material is homogenous across measurement sites), and can thereby be determined based on:

$$Rs=(T1a \cdot Rca \cdot Rcb-T1b \cdot Rca \cdot Rcb)/(T1b \cdot Rca-T2b \cdot Rca-T1a \cdot Rcb+T2a \cdot Rcb)$$

$$Tc=(T1a \cdot T1b \cdot Rca-T1a \cdot T2b \cdot Rca-T1b \cdot T1a \cdot Rcb+T2a \cdot T1b \cdot Rcb)/(T1b \cdot Rca-T2b \cdot Rca-T1a \cdot Rcb+T2a \cdot Rcb)$$

where T1a, T2a, T1b, T2b can be for collected temperature data (e.g., in Block S110), and Rca and Rcb can be predetermined and/or dynamically estimated in real-time. Determining Rca, Rcb, and/or other suitable thermal resistances can include: selecting materials with known thermal resistances, transient approaches (e.g., needle probes; transient plane source; transient line source; laser flash; time-domain thermoreflectance; etc.), steady-state approaches, and/or any other suitable approaches. In an example, the method 100 can include: determining a first thermal resistance for a first insulating material thermally coupled to a first set of temperature sensors associated with a first heat flux channel; determining a second thermal resistance for a second insulating material thermally coupled to a second set of temperature sensors associated with a second heat flux channel; determining additional thermal resistances for additional insulating material (e.g., a third thermal resistance for a third insulating material thermally coupled to a third set of temperature sensors; thermal resistances for additional insulating material thermally coupled to the first or second set of temperature sensors; etc.); and extracting a perfusion parameter based on the thermal resistances and temperature data.

In this variation of Block S120, instability can occur at T1a=~T1b. In an example of avoiding this or other potential instabilities, temperature measurements can be made at least substantially equal (e.g., T2a=~T2b, such as for the temperature sensors arrange proximal the end regions of the heat flux channels, etc.), while having varying thermal resistances (e.g., Rca=/=Rcb, such as for the respective insulating materials, etc.). In another example of avoiding this or other potential instabilities, thermal resistances can be made at least substantially equal (e.g., Rca=Rcb), while ensuring varying temperature measurements (e.g., T2a=/=T2b). In this example, Rs and Tc can be determined based on:

$$Rs=Rc(T1a-T1b)/(T2a+T1b-T1a-T2b)$$

$$Tc=(T2a*T1b-T1a*T2b)/(T2a+T1b-T1a-T2b)$$

where Rc=Rca=Rcb, and where predetermined characterizations of Rc can facilitate absolute measures of perfusion parameters, and where predetermined fixed selections of Rc can facilitate consistent, relative measurements of Rs (e.g., which can be used for determining absolute measurements of Tc, etc.). Pursuing substantially equal thermal resistances can facilitate improvements in manufacturing (e.g., precision construction in relation to designing and manufacturing the insulation materials in relation to their corresponding heat flux channels), analysis (e.g., circumventing measurement of relative insulation metrics across measurements sites; etc.) In an example, as shown in FIG. 5, an additional insulating material, corresponding to Rm, can be thermally coupled to a temperature sensor (e.g., corresponding to T2b; to T2a) to force different temperature measurements (e.g., T2a=/=T2b). In a specific example, Block S120 can include: determining an auxiliary thermal resistance for an auxiliary insulating material thermally coupled to a temperature sensor (e.g., corresponding to T2b), and extracting the perfusion parameter based on the auxiliary thermal resistance (e.g., where the perfusion parameter can be extracted without needing the Rm value to be used in equations; where Rm can alternatively be used in suitable equations for perfusion and/or other parameter determination; etc.), the temperature data (e.g., where temperature data for the temperature sensor thermally coupled to the auxiliary insulating material is affected based on the auxiliary thermal resistance; etc.), and the first and the second thermal resistances (e.g., corresponding to Rca and Rcb, which can be equal, etc.). For an auxiliary insulating material thermally coupled to a temperature sensor corresponding to T2b, as shown in FIG. 5, T2b can be characterized as an intermediary temperature between T2a and T1b, such as described by:

$$T2b=T1b+(T2a-T1b)/(Rcb+Rm).$$

In another example, temperature sensors (e.g., corresponding to T2b) can be thermally coupled to, physically coupled to, and/or otherwise associated with ambient temperatures, heat sinks (e.g., where a temperature sensor corresponding to T2a can be coupled with a large heat sink, and a temperature sensor corresponding to T2b can be coupled with a small heatsink or no heatsink; etc.), other thermal features, and/or any other suitable components. Additionally or alternatively, instabilities can be circumvented in any suitable manner.

In another variation, the Block S120 can include determining an overall perfusion parameter (e.g., a combined perfusion parameter such as through averaging, other combination techniques, etc.) based on individual perfusion parameters (e.g., historic and/or reference perfusion parameters, such as under similar contextual conditions for the same or different user, etc.). In an example, individual perfusion parameters can be determined from different pairs (e.g., permutations) of measurement sites (e.g., where one or more temperature monitoring devices include at least three measurements sites, etc.). However, determining perfusion parameters based on multiple measurement sites can be performed in any suitable manner.

Figure 6:
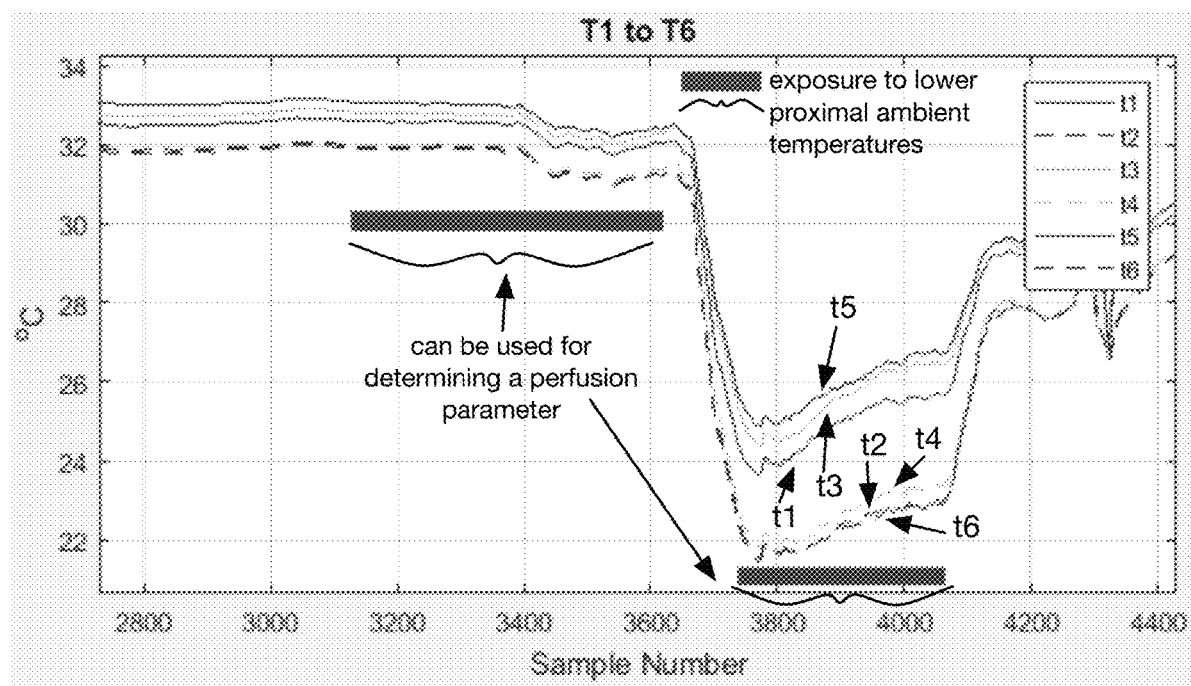
FIG. 6 depicts a graph representation of a variation for time-shift estimation.

Additionally or alternatively, determining perfusion parameters (and/or other parameters) can be based on a single measurement site (e.g., through time-shift estimation), which can function to facilitate coarse estimation, low power estimation, contact resistance estimation and/or validation, accounting for variable skin contact resistance, accounting for sample non-homogeneity, and/or other suitable purposes. Temperature data collected over a time period (and/or multiple time periods) in relation to single measurement site (e.g., a single heat flux channel thermally coupled to a set of temperature sensors) can be used under the assumption of negligible change to Tc and Rs during the time period. In a variation, differences across time shifts can be used in describing:

$$T1b(k)=T1a(k+N),$$

$$T2b(k)=T2a(k+N)$$

where N is a determined time shift, where:

$$Rs=Rc(T1a-T1b)/(T2a+T1b-T1a-T2b)$$

$$Tc=(T2aT1b-T1aT2b)/(T2a+T1b-T1a-T2b)$$

and where Rc=Rca=Rcb given the usage of the same measurement site. In an example, as shown in FIG. 6, temperature data collected prior to and after the transition of a sharp decrease in temperature can be used in calculating a perfusion parameter. In this example or other examples, Block S120 can include applying different approaches to determining perfusion parameters based on steady-state conditions or transient conditions (e.g., detected based on temperature data collected from temperature sensors, motion sensor data, and/or other contextual data; where different perfusion models can be applied, such as applying a simple multi-site model during steady-state conditions, and applying a transient state model during transient conditions, where the different models can include any suitable approaches described herein; etc.). In a specific example, the method 100 can include: collecting first temperature data for a first time period from a set of temperature sensors thermally coupled to a heat flux channel corresponding to a measurement site; collecting second temperature data for a second time period from the set of temperature sensors; and extracting a perfusion parameter associated with the first and the second time periods based on the first and the second temperature data. In another example, the method 100 can include: collecting a continuous time series of temperature data during a transient event, from one or more sets of temperature sensors thermally coupled to corresponding heat flux channels; and apply best-fit regressions to various finite-element, or continuous models, and/or any other suitable models described herein, either in real-time or post-processed, to determine perfusion parameters. However, determining perfusion parameters based on a single measurement site can be performed in any suitable manner, and Block S120 can be performed in any suitable manner.

3.3 Determining a Physiological Metric.

Block S130 recites: determining a physiological metric based on the perfusion parameter functions to determine a metric associated with a user condition, which can facilitate characterization and/or inform improvement of a state of the user condition of the user. Physiological metrics preferably include core body temperature measurements, which can include: core body temperature associated with a temporal indicator (e.g., current core body temperature, core body temperature for a time, for a time period, etc.), an overall core body temperature (e.g., determined based on individual core body temperatures measured with different temperature sensors, with different combinations of heat flux channels, with different temperature monitoring devices; etc.), a series of core body temperatures (e.g., a time series of core body temperature measurements for a time series; core body temperature trends, patterns, variations, etc.), core body temperature for steady-state conditions, core body temperature for transient conditions, modified core body temperature measurements (e.g., normalized based on circadian variation, based on contextual variables, etc.), and/or any other suitable measurements associated with core body temperature. In an example, Block S130 can include determining a series of core body temperature measurements for a set of time periods (e.g., based on temperature data, perfusion parameters, and/or other suitable data for the particular time period, etc.).

Regarding Block S130, determining core body temperature measurements is preferably based on one or more perfusion parameters, temperature data, and/or associated thermal properties (e.g., channel thermal resistances, etc.), but can additionally or alternatively be based upon any suitable data. In a variation, Block S130 can include applying (e.g., generating, training, storing, retrieving, executing, etc.) a data-driven core temperature model for steady-state estimation (e.g., during steady-state conditions, such as during an undisturbed state, during an core body temperature equilibrium state, etc.). A plurality of datasets including varying temperature sensor data, contextual data, and/or other suitable data (e.g., datasets with randomly swept core body temperature, air temperature, cutaneous region/skin thickness, etc.) can be processed to generate the core-temperature model. In an example, the method 100 can include: collecting reference temperature data for a set of users from a set of temperature monitoring devices, where each temperature monitoring device from the set of temperature monitoring devices includes a set of heat flux channels, where the reference temperature data is associated with at least one of different steady-state conditions and different transient conditions; generating a core temperature model based on the reference temperature data; and determining a core body temperature measurement for a current user based on the core temperature model and temperature data collected in association with the current user. In a specific example, temperature data leveraged in a data-driven model for steady-state estimation, and/or in any other suitable models can include temperature data collected from eight temperature sensors, which can include two pairs of temperature sensors corresponding to two heat flux channels, a cross-talk temperature sensor arranged between the heat flux channels, and three heat gradient temperature sensors (e.g., arranged at arcuate positions separated by 120 degrees at the substrate of the substrate and/or other suitable component of the temperature monitoring device, etc.). In another specific example, Block S130 can include performing statistical estimation of core body temperature measurements using the core temperature model, such as through ordinary least squares, non-negative least squares regression, principal components analysis, ridge regression, other suitable regression techniques (e.g., where the datasets used to develop the model can be used in determining coefficients robust across different conditions; etc.), and/or any other suitable approaches described herein. In an example, regression analysis and/or other suitable approaches can be applied to a continuous time series of temperature data (e.g., collected in association with a plurality of heat flux channels) and/or other suitable data (e.g., contextual data; steady state conditions; transient conditions; etc.) to determine core body temperature measurements, perfusion parameters, and/or other suitable parameters best fitting the data. However, determining physiological metrics with a model for steady-state estimation can be performed in any suitable manner.

Figure 8:
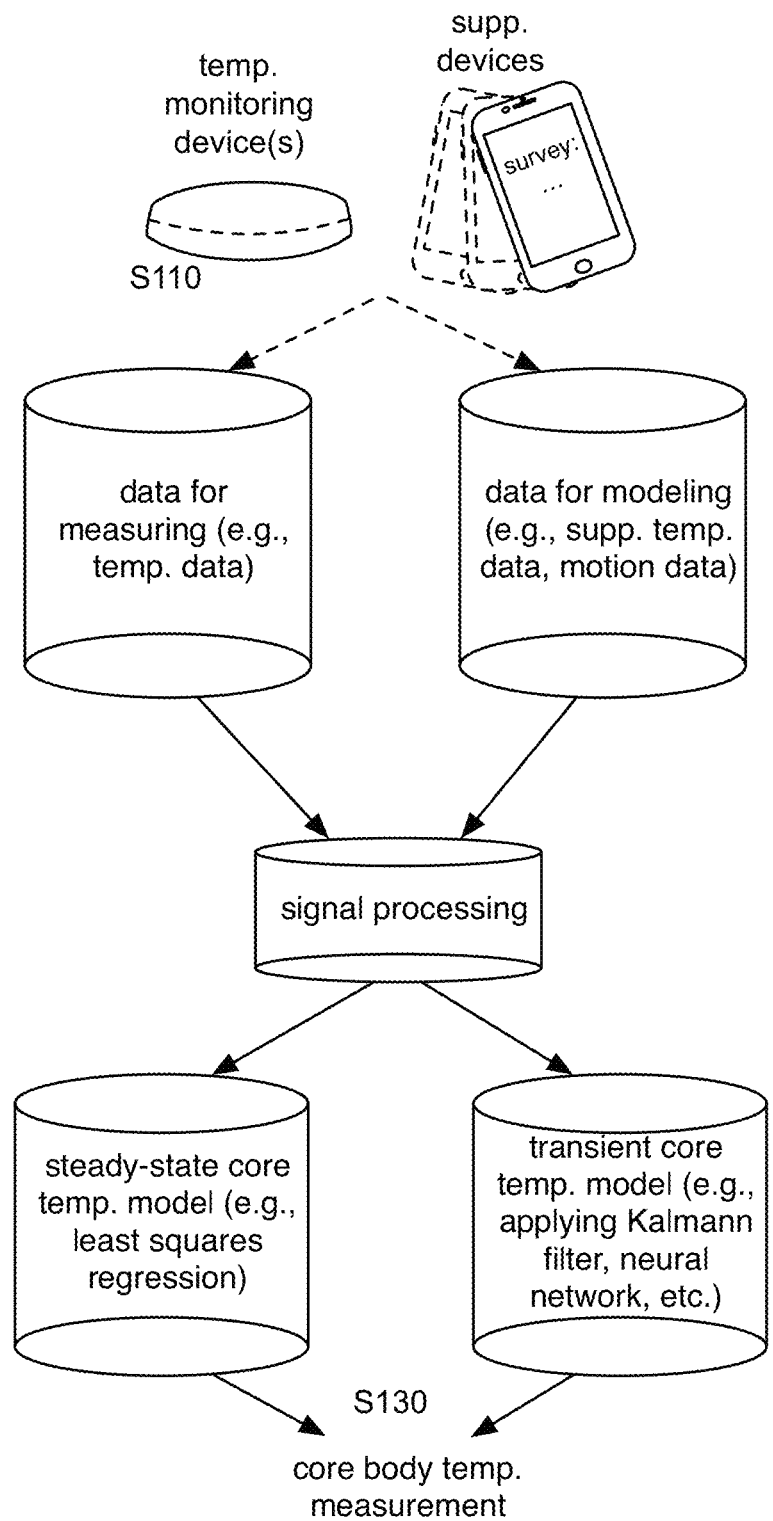
FIG. 8 depicts a schematic representation of an embodiment of a method for characterizing core body temperature.

In another variation, Block S130 can include applying a data-driven core temperature model for transient estimation (e.g., during transient conditions, such as during a disturbed state, such as when core body temperature is not in an equilibrium state, etc.), which can be used for determining accurate core body temperature measurements during transient conditions (e.g., which can be used for real-time, continuous monitoring; healthcare applications for detecting spikes in core body temperature; etc.). As shown in FIG. 8, the core temperature model can include applying any one or more of: Kalmann filtering, adaptive least mean squares (LMS) filtering, inverse transfer function estimation tools, neural network and/or other deep learning approaches, other fuzzy logic approaches, and/or any other suitable approaches described herein. However, determining physiological metrics with a model for transient estimation can be performed in any suitable manner.

In another variation, Block S130 can include selecting from (e.g., between) steady-state core temperature models, transient core temperature models, and/or other suitable models for determining physiological metrics. Model selection can be based on: contextual data (e.g., motion sensor data, location data, etc.), temperature data, other varying conditions, and/or any other suitable data. For example, the method 100 can include collecting supplemental data sampled for the time period from a sensor (e.g., accelerometer) of the temperature monitoring device; selecting between a steady-state core temperature model and a transient core temperature model based on the supplemental data (e.g., based on the accelerometer indicating physical activity satisfying a threshold condition; etc.); and determining the core body temperature measurement based on the selected core temperature model and the collected temperature data (e.g., in Block S110). However, selecting between models can be performed in any suitable manner.

Regarding Block S130, additionally or alternatively, physiological metrics can include any one or more of: skin parameters (e.g., cutaneous region/skin thickness, galvanic skin response, skin temperature, etc.), cardiovascular parameters (e.g., vasodilation, vasoconstriction, vasocongestion, blood pressure parameters, instantaneous blood pressure, blood pressure variability, instantaneous heart rate, heart rate variability, average heart rate, resting heart rate, heartbeat signature, pulse rate metrics etc.), other temperature parameters (e.g., heat loss, other types of temperature data, etc.), respiration parameters (e.g., respiration rate, depth of breath, shallowness of breath, inhalation-to-exhalation ratio, thoracic variations, tidal volume, inspiratory flow, expiratory flow, work of breathing, phase angle, respiratory waveform morphology, etc.), data regarding analytes detectible in biological fluids (e.g., blood, sweat, interstitial fluid, chime, saliva, serum, etc.), and/or any other suitable metrics.

In a variation, Block S130 can include determining a cutaneous region/skin thickness parameter (e.g., effective skin thickness, vascularity, etc.), such as a cutaneous region/skin thickness parameter associated with a time period (e.g., corresponding to temperature data, to a calculated core body temperature, etc.) based on the temperature data and the heat flux channel thermal resistances (e.g., for a dual-flux system; for a multi-flux system where different pairs of heat flux channels can be leveraged in determining individual physiological metrics that can be combined into an overall physiological metric, etc.), where the cutaneous region/skin thickness parameter can be determined without knowing core body temperature. In an example, determining the cutaneous region/skin thickness can be based on:

$$Tc=T1+k1(T1-T2)$$

$$Tc=T3+k2(T3-T4)$$

where $k=R_{THERMAL\ (skin)}/R_{THERMAL\ (channel)}$, leading to simultaneous equations of:

$$Tc=T1+(R_{TH(skin)}/R_{TH(channel\ 1)})*(T1-T2)$$

$$Tc=T3+(R_{TH(skin)}/R_{TH(channel\ 2)})*(T3-T4)$$

where T1, T2, T3, and T4 correspond to a first, second, third, and fourth temperature sensor (e.g., where the first and second temperature sensors correspond to a first heat flux channel, and the third and fourth temperature sensors correspond to a second heat flux channel) and can be measured, and where $R_{TH(channel\ 1)}$ and $R_{TH(channel\ 2)}$ correspond to channel thermal resistances for the first and the second heat flux channel, respectively, and can be characterized. With an assumption of equal Tc across measurement sites, the simultaneous equations can be solved for $R_{TH\ (skin)}$, the increase of which can be detected as a thicker skin parameter value and vice versa. However, calculating cutaneous region/skin thickness parameters can be performed with any suitable model and in any suitable manner.

In another variation, Block S130 can include determining a heat loss parameter, such as a heat loss parameter associated with the time period (e.g., corresponding to a core body temperature measurements, corresponding to a skin thickness parameter measurement), such as based on a core body temperature measurement and a cutaneous region/skin thickness parameter. In an example, determining a heat loss parameter can be based on an analogy to voltage drop, such as described by:

$$V=IR$$

$$V=(Tc-T1)$$

$$R=R_{TH(skin)}$$

$I$=rate of heat flow $$I=(Tc-T1)/R_{TH\ (skin)}$$

Additionally or alternatively, determining the heat loss parameter can be performed without Tc and $R_{TH\ (skin)}$, such as through assuming heat flow of skin equals heat flow through the temperature monitoring device, which can enable calculation by: $(T1-T2)/R_{TH(channel\ 1)}=I$. However, determining heat loss can be performed with any suitable model and in any suitable manner.

In another variation, Block S130 can include determining a skin temperature parameter, such as based on temperature data from temperature sensors arranged proximal measurement sites (e.g., corresponding to T1 and T3; temperature sensors arranged at beginning regions of heat flux channels; etc.), where the temperature data can act as proxies for skin temperature. However, determining skin temperature parameters can be performed with any suitable model in any suitable manner. In another variation, Block S130 can include determining a galvanic skin response (GSR) parameters, such as based on measurements associated with heat collectors (e.g., magnets arranged between the housing and a temperature sensor; other thermally conductive components; etc.) of the temperature monitoring devices; however, determining GSR parameters can be performed with any suitable model in any suitable manner.

In variations, Block S130 (and/or other portions of the method 100) can include applying physiological metric models (and/or other suitable models) including any one or more of: probabilistic properties, heuristic properties, deterministic properties, and/or any other suitable properties. The models can be run or updated: once; at a predetermined frequency; every time an instance of an embodiment of the method and/or subprocess is performed; every time an unanticipated measurement value (e.g., unexpected temperature data, unexpected accelerometer data, etc.) is received; and/or at any other suitable frequency. The models can be run or updated concurrently with one or more other models, serially, at varying frequencies, and/or at any other suitable time. In examples, Block S130 and/or other potions of the method 100 (e.g., in relation to any suitable models) can employ machine learning approaches including any one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked autoencoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and/or any suitable form of machine learning algorithm. Additionally or alternatively, applying physiological metric models can be performed in any suitable manner. However, determining physiological metrics can be performed in any suitable manner.

3.4 Characterizing a User Condition.

Embodiments of the method 100 can additionally or alternatively include Block S140, which recites: characterizing one or more user conditions based on one or more physiological metrics. Block S140 can function to characterize (e.g., detect, diagnose, evaluate, etc.) one or more user conditions and/or associated treatments (e.g., over time, such as for evaluating treatment efficacy and updating treatments, etc.) based on outputs from portions of the method 100. Characterizing the user condition can include one or more of: determining user condition-associated parameters informative of the user condition (e.g., risk of user condition), detecting the user condition, evaluating the user condition (e.g., a severity of the user condition), presenting associated information (e.g., through notifications to users, care provider, and/or other entities, etc.), and/or any other suitable process. Block S140 preferably includes characterizing a fever condition, but any suitable user conditions can be characterized. Characterizing user conditions is preferably based on one or more core body temperature measurements, but can additionally or alternatively be based on one or more of: time (e.g., menstrual phase, circadian rhythm, etc.), other physiological metrics, perfusion parameters, temperature data, supplementary sensor data (e.g., motion sensor data, location data, biometric data, from temperature monitoring devices, user computing devices, etc.), supplementary medical device data, user data (e.g., demographic data such as age, gender, nationality, ethnicity; user behavior data such as physical activities, interests, life events, social media data; medical data such as medications including birth control; data collected through surveys, querying third party databases; etc.). In an example, Block S140 can be include detecting the fever-associated condition based on the skin temperature parameter, the galvanic skin response parameter, the core body temperature measurement, the cutaneous region/skin thickness parameter, and the heat loss parameter. In a specific example, detecting a fever-associated condition can be based on determining an increasing core body temperature measurement, a decreasing heat loss, and an increasing cutaneous region/skin thickness parameter (e.g., as opposed to an indication of exercising based on an increasing core body temperature and heat loss, but a decreasing cutaneous region/skin thickness parameter, etc.).

In a variation, Block S140 can include detecting different stages of infection (and/or corresponding fever) based on different outputs of the method 100. For example, a physiological response of trying to reach a new set point after infection (e.g., causing the hypothalamus to increase its set point) can be indicated by an increase in core body temperature measurements, an increase in vasoconstriction, a decrease in skin temperature parameters, a decrease in heat loss parameters, an increase in cutaneous region/skin thickness parameters, a decrease in GSR parameters, an increase in shivering (e.g., as determined by accelerometer data), and/or any other suitable observations. In another example, a subsequent physiological response of the set point dropping after the new set point is reached can be indicated by decreasing core body temperature measurements, vasodilation, increasing skin temperature measurements, increasing heat loss parameters, decreasing cutaneous region/skin thickness parameters, increasing GSR parameters, sweating (e.g., as detected by measuring GSR, etc.), and/or other suitable observations. However, detecting different stages of any suitable user condition can be performed in any suitable manner.

Figure 9:
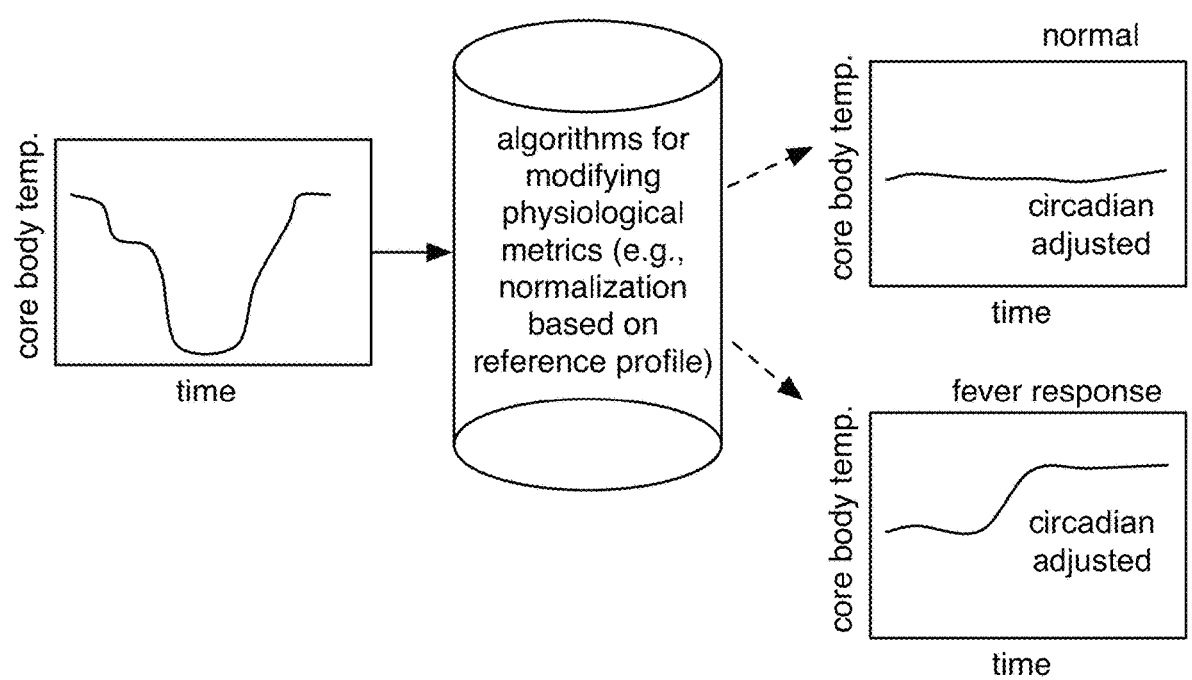
FIG. 9 depicts a schematic representation of a variation of modifying core body temperature measurements.
Figure 10:
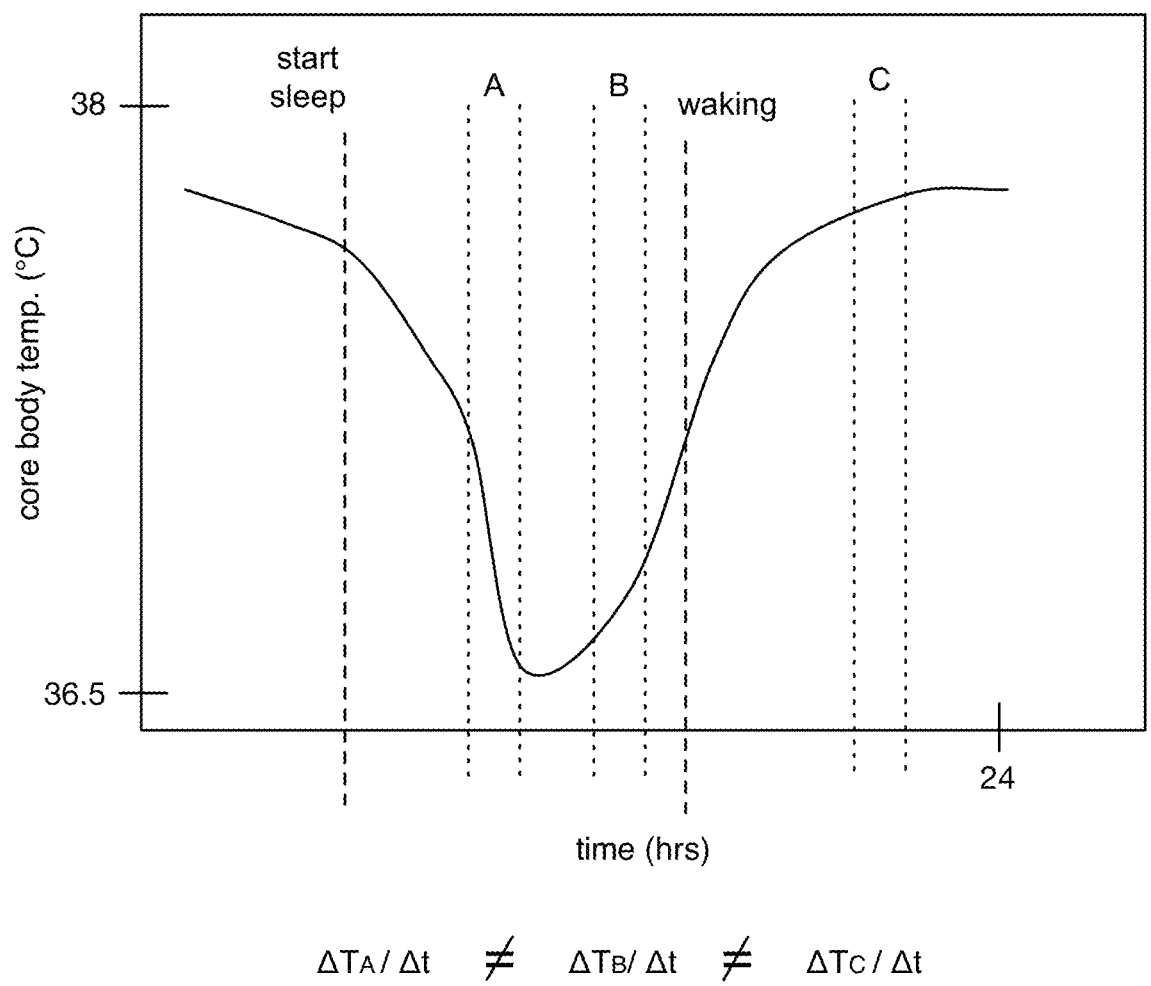
FIG. 10 depicts a schematic representation of a variation of modifying core body temperature measurements.

In another variation, as shown in FIG. 9, Block S140 an include modifying (e.g., normalizing, etc.) physiological metrics (e.g., for improving suitability of the physiological metrics in indicating and/or otherwise characterizing user conditions, such as in relation to immunocompromised patients where variations in core body temperature relative normal core body temperatures can be indicative of user conditions; for avoiding false negatives; avoiding false positives; accounting for variations to facilitate reliable user condition characterization, etc.). In examples, Block S140 can include modifying core body temperature measurements based on circadian rhythm influences on core body temperature measurements (e.g., where core body temperature can vary depending on time of day; core body temperatures can be lower in the hours before waking, higher in the later afternoon and/or early evening; etc.), circamensal rhythm (e.g., accounting for higher average core body temperatures such as 0.2° C.-0.5° C. in the post-ovulatory phase of a menstrual cycle, where larger correction values can be used during the second half of the menstrual cycle, etc.), age (e.g., accounting for decreases of circadian variation in core body temperature with age; accounting in time shifts for expected circadian fluctuations, such as where teenager can experience expected core body temperature fluctuations two hours later than adults; etc.), fitness (e.g., accounting for increased variations for users with higher fitness levels, etc.), circannual rhythm (e.g., accounting for seasonal affects, weather affects, date, other seasonal data, etc.), location (e.g., accounting for variability with temperature, etc.), medication (e.g., accounting for effect of birth control in suppressing circamensal rhythm and increasing core body temperature, etc.), dietary behavior (e.g., number of consumed calories, time of consumption, caffeine intake that can delay core temperature decrease at night, etc.), sleep behavior (e.g., sleep disruption affecting natural circadian rhythm), melatonin levels, cortisol levels, light exposure, other user behaviors (e.g., smoking, etc.), and/or any suitable data described herein, and/or other criteria (e.g., medical reference metrics, such as a fever definition of core body temperature over 38° C., etc.). Modifying core body temperature measurements can include performing a time-weighted temperature correction based on reference profiles (e.g., a reference template) indicative of circadian affect on core body temperature (e.g., patterns, trends, variations, and/or other insights that can be accounted for, etc.). Reference profiles can be generated on an individual user basis (e.g., using historic data for the user as a personalized reference template for modifying future physiological metrics determined for the user, etc.), multiple user basis (e.g., using data from other users to generate a reference profile, which can be applied to specific user subgroups, etc.), predetermined profile basis (e.g., generating composite reference profiles suited for different varying conditions, etc.), and/or any other suitable basis. Normalization based on reference profiles can include addition of larger average temperature values during time periods of fast temperature decrease (e.g., during sleep, etc.), subtraction of larger average temperature values during time periods of faster temperature increase (e.g., during waking, etc.), smaller average temperature value additions and subtractions during less rapid changes of core body temperature, and/or any other suitable magnitude of adjustments based on any suitable criteria. In an example, as shown in FIG. 10, $$\Delta T_A/\Delta t_A, \Delta T_B/\Delta t_B, \Delta T_C/\Delta t_C$$

can be accounted for through normalization.

In a specific example, for a set of core body temperature measurements readings associated with a time period corresponding to an average increase in core body temperature of 0.05° C., the core body temperature measurements can be adjusted by −0.05° C. In another specific example, the method 100 can include collecting reference temperature data sampled for a reference time period for the user from the first and the second set of temperature sensors (e.g., corresponding to a first and a second heat flux channel); determining a reference series of core body temperature measurements over the reference time period for the user based on the reference temperature data; generating a reference circadian profile for the user based on the reference series of core body temperature measurements; determining a core body temperature measurement for a current time period; and modifying the core body temperature measurement for the current time period based on the reference circadian profile (and/or other suitable data, such as motion sensor data sampled from a motion sensor of a mobile computing device, location data sampled from a location sensor of the mobile computing device, etc.).

In another variation, Block S140 can include applying a user condition model associated with any suitable properties, algorithms, and/or approaches described herein. In an example, the method 100 can include generating a user condition model based on reference core body temperature measurements associated with a user condition and determined for a set of reference users with a set of temperature monitoring devices; determining a series of core body temperature measurements for the current user for a set of time periods based on temperature data and/or other suitable data, and characterizing the user condition based on the series of core body temperature measurements and the user condition model. In another variation, characterizing user conditions can include facilitating treatment provision, such as through providing notifications to users and/or care providers (e.g., at corresponding devices and/or interfaces), providing treatments through the temperature monitoring device and/or any other suitable device, providing outputs for generating control instructions for treatment devices, and/or through any other suitable means.

In relation to Block S140, characterizing user conditions is preferably performed in at least substantially real-time (e.g., within a time period associated with a core body temperature measurement used in characterizing the user condition; during a time period in which the temperature monitoring device is coupled to the user; etc.), but can be performed at predetermined time intervals, in response to trigger conditions (e.g., collection of temperature data; determination of physiological metrics; time of day such as when the user is awake; etc.), and/or at any suitable time and frequency. However, characterizing user conditions can be performed in any suitable manner.

Although omitted for conciseness, the embodiments include every combination and permutation of the various system components and the various method processes, including any variations, examples, and specific examples, where the method processes can be performed in any suitable order, sequentially or concurrently using any suitable system components.

The system and method and embodiments thereof can be embodied and/or implemented at least in part as a machine configured to receive a computer-readable medium storing computer-readable instructions. The instructions are preferably executed by computer-executable components preferably integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the embodiments without departing from the scope defined in the following claims.

We claim:

1. A method for characterizing core body temperature for a user, the method comprising:
    determining a series of core body temperature measurements for a set of time periods, wherein determining the series of core body temperature measurements comprises, for each of the time periods in the set of time periods:
        collecting first temperature data sampled for the time period from a first set of temperature sensors thermally coupled to a first heat flux channel of a temperature monitoring device, wherein the first temperature data is indicative of first temperature change through the first heat flux channel during the time period;
        collecting second temperature data sampled for the time period from a second set of temperature sensors thermally coupled to a second heat flux channel of the temperature monitoring device, wherein the second temperature data is indicative of second temperature change through the second heat flux channel during the time period;
        collecting reference temperature data sampled for a reference time period for the user from the first and the second set of temperature sensors;
        determining a reference series of core body temperature measurements over the reference time period for the user based on the reference temperature data;
        generating a reference circadian profile for the user based on the reference series of core body temperature measurements; and determining a core body temperature measurement for the time period based on the first and the second temperature data, wherein the series of core body temperature measurements comprises the core body temperature measurement;

wherein determining the series of core body temperature measurements comprises, for each of the time periods in the set of time periods, modifying the core body temperature measurement for the time period based on the reference circadian profile; and wherein modifying the core body temperature measurement for the time period comprises:

collecting motion sensor data sampled for the user from a motion sensor of a mobile computing device;

collecting location data sampled for the user from a location sensor of the mobile computing device; and modifying the core body temperature measurement for the time period based on the location data and the motion sensor data;

characterizing a user condition for the user based on the series of core body temperature measurements associated with the set of time periods, wherein the user condition comprises an early detected fever; and transmitting a notification to the user based on the early detected fever, wherein the notification comprises a message prompting treatment provision of the early detected fever, wherein the treatment provision comprises a recommended prescription.

2. The method of claim 1, further comprising:

collecting reference temperature data for a set of users from a set of temperature monitoring devices, wherein each temperature monitoring device from the set of temperature monitoring devices comprises a set of heat flux channels, wherein the reference temperature data for the set of users is associated with at least one of different steady-state conditions and different transient conditions; and generating a core temperature model based on the reference temperature data for the set of users, wherein determining the core body temperature measurement for the time period comprises determining the core body temperature measurement based on the core temperature model and the first and the second temperature data.

3. The method of claim 2, wherein determining the series of core body temperature measurements comprises, for each of the time periods in the set of time periods:

collecting supplemental temperature data sampled for the time period from a set of supplemental temperature sensors, wherein the supplemental temperature data is indicative of a heat gradient across the temperature monitoring device and cross-talk between the first and the second heat flux channels; and determining the core body temperature measurement for the time period based on the core temperature model, the supplemental temperature data, and the first and the second temperature data.

4. The method of claim 3, wherein determining the series of core body temperature measurements comprises, for each of the time periods in the set of time periods:

collecting third temperature data sampled for the time period from a third set of temperature sensors thermally coupled to a third heat flux channel of the temperature monitoring device; and determining the core body temperature measurement based on the core temperature model, the supplemental temperature data, and the first, the second, and the third temperature data.

5. The method of claim 1, wherein determining the series of core body temperature measurements comprises, for each of the time periods in the set of time periods:

collecting supplemental data sampled for the time period from a sensor of the temperature monitoring device;

selecting between a steady-state core temperature model and a transient core temperature model based on the supplemental data; and determining the core body temperature measurement based on the selected core temperature model and the first and the second temperature data.

6. The method of claim 1, wherein determining the series of core body temperature measurements comprises, for each of the time periods in the set of time periods, extracting a first perfusion parameter associated with the time period based on the first and the second temperature data, wherein determining the core body temperature measurement for the time period comprises determining the core body temperature measurement based on the first perfusion parameter.

7. The method of claim 6, further comprising:

collecting first subsequent temperature data for a first subsequent time period from the first set of temperature sensors, wherein the first subsequent time period is subsequent to the set of time periods;

collecting second subsequent temperature data for a second subsequent time period from the first set of temperature sensors, wherein the second subsequent time period is subsequent to the set of time periods;

extracting a second perfusion parameter associated with the first and the second subsequent time periods based on the first and the second subsequent temperature data; and determining a subsequent core body temperature measurement associated with the first and the second subsequent time periods based on the second perfusion parameter.

* * * * *